(12) United States Patent
Bertha

(10) Patent No.: US 7,285,291 B2
(45) Date of Patent: Oct. 23, 2007

(54) METHOD FOR OBTAINING AN ANTI-TUMOR SUBSTANCE FROM EVEN-TOE HOOFED MAMMALS

(75) Inventor: András Bertha, Budapest (HU)

(73) Assignee: Medveritas Intellectual Property Holding S.A. (PA)

( * ) Notice: Subject to any disclaimer, the term of this patent is extended or adjusted under 35 U.S.C. 154(b) by 0 days.

(21) Appl. No.: 10/501,438

(22) PCT Filed: Jan. 15, 2003

(86) PCT No.: PCT/HU03/00004

§ 371 (c)(1),
(2), (4) Date: Jul. 13, 2004

(87) PCT Pub. No.: WO03/059364

PCT Pub. Date: Jul. 24, 2003

(65) Prior Publication Data

US 2005/0025836 A1    Feb. 3, 2005

(30) Foreign Application Priority Data

Jan. 15, 2002   (HU) .................................. 0200172

(51) Int. Cl.
*A61K 35/20*   (2006.01)
*C07K 1/14*    (2006.01)
*C07K 14/435*  (2006.01)

(52) U.S. Cl. ...................... 424/535; 530/424; 530/426; 530/350

(58) Field of Classification Search ..................... None
See application file for complete search history.

(56) References Cited

U.S. PATENT DOCUMENTS

2005/0152985 A1* 7/2005 Janusz et al. ............... 424/535

FOREIGN PATENT DOCUMENTS

WO    WO 0040256    7/2000

OTHER PUBLICATIONS

Cancer Principles & Practice of Oncology, 6th Ed., De Vita et al., eds., Lippincott Williams & Wilkins, Philadelphia, 2001, pp. 308-312.*
XP-002067385 Zusatzliche Behandlung des Kollumkarzinom im III. Stadium mit inkubiertem Leukamieblut nach Strahlentheraple Zentralblatt fur Gynakologie vol. 93 pp. 634-639 (1971).

* cited by examiner

*Primary Examiner*—Rebecca E. Prouty
*Assistant Examiner*—Rosanne Kosson
(74) *Attorney, Agent, or Firm*—Foley & Lardner, LLP

(57) ABSTRACT

Method for obtaining an anti-tumor substance from even-toe hoofed mammals (artio-dactylous animals) having leucosis, and according to a first alternative, the substance is obtained from the lipid-free blood plasma fraction of the animal, and the blood is taken from a pregnant female donor animal being in the 2nd or 3rd period of pregnancy up to at most the beginning of the first week preceding delivery. According to a second alternative the substance is obtained from the colostrum of the female donor animal, being preferably cow or sheep.

6 Claims, No Drawings

METHOD FOR OBTAINING AN ANTI-TUMOR SUBSTANCE FROM EVEN-TOE HOOFED MAMMALS

This application is the U.S. national phase of International Application No. PCT/HU 03/00004, filed on Jan. 15, 2003, which claims priority to Hungarian Application No. P0200172, filed on Jan. 15, 2002.

The invention relates to a method for obtaining an anti-tumor substance from even-toe hoofed mammals (artiodactylous animals) having leucosis.

The international publication WO 00/40256 relates to the tumor inhibiting effects on different types of tumors of the blood plasma obtained from patients suffering from acute leukemia. In the specification several sets of experiments were disclosed, wherein the applied substance resulted in an improvement by 20% compared to the control group. Such an improvement constitutes the lower limit of what can be qualified as significant.

In my Hungarian patent application P 0002597 I have recognized that from the lipid-free blood plasma fraction of even-toe hoofed mammals (artiodactylous animals) having leucosis a substantially more efficient tumor-inhibiting effect can be obtained than from what can be obtained from leukemic blood, and a method was disclosed for obtaining the plasma component responsible for the effect.

The effect was confirmed by the experiments carried out with animals having different types of tumor disclosed in the cited patent application.

In the published international patent application WO 02/07739 claiming the priority of the cited Hungarian patent application further experiments with animals were disclosed for verifying the tumor-inhibiting effect, which related to further tumor types, and the effect was demonstrated in case of different ways of administering the active substance (intramuscular, subcutane, intraperitonial and per os).

In view of the outstanding tumor-inhibiting effect, both the preparation method and efficiency of obtaining the active substance have great significance. Besides the possibility of obtaining the material from animal blood one has to examine all other ways by which one can arrive at the same substance.

The object of the invention is to provide a more efficient method for obtaining the active substance described in the cited patent applications.

I have recognized that the concentration of the tumor-inhibiting substance (as an immune antibody) is changing in the blood of the animal during pregnancy, furthermore the substance appears in the milk immediately following the delivery. The milk provided during the first feeding after delivery and during a few number of subsequent feeding is referred to as colostrum.

In the animal organism the immune system makes sure that the newborn obtains the available antibodies of the immune system of the suckler by consuming the colostrum during the first few lactation in a concentrated way, whereby it will be resistant against outer infections. In the blood of the suckler the concentration of the antibodies will thereby decrease in the period just following the delivery, and these materials will be concentrated in the colostrum. This phenomenon can be observed in the first few weeks of lactation.

According to the first aspect of the invention, the colostrum of even-toe hoofed mammals (artiodactylous animals) primarily cattle (cows) that have leucosis is utilized for obtaining the active substance responsible for the tumor-inhibiting effect.

According to the second aspect of the invention the fact is utilized that the concentration of the antibodies in the blood of the pregnant animal increases during the medium and last third of pregnancy, and the active substance is taken from the blood of donor pregnant animals being in such state of pregnancy. The most preferred animals are cattle and sheep. The utilizable period ends because in the last days of pregnancy and during the first few days of lactation the antibody level in the blood decreases and it increases in the colostrum to a high level.

The active substance is obtained from the colostrum by using a separation method similar to the one disclosed in the above referred patent application wherein the starting material was the blood plasma of the animal.

The separation method comprises preferably the following steps:

1) The colostrum is shaken with a 1:1 mixture of i-propyl alcohol and chloroform of identical volume on room temperature through 8 hours in a shaker machine
2) The material is centrifuged at a speed of 10000 rev/min through 20 minutes in a cooled state.
3) The floating upper layer and the medial crust layer are separated (the organic phase is spilled), and the rest of the material is diluted with the addition of a 1:1 mixture of chloroform and benzyl alcohol to take the original volume and shaken through 8 hours with a shaker machine.
4) The material is stored through 10 hours at a temperature of +2-4° C.
5) The material is centrifuged just as in step 2 and the organic phase is spilled.
6) The floating upper layer is deep-frozen and freeze-dried and by means of a physiologic saline solution the required concentration is adjusted. This product was used for efficiency examination of tumorous mice and it has proven biologically active.
7) The central, jelly-like crust layer (in step 3) is frozen and freeze-dried, and the treatment is continued as in step 6. The so-obtained material was biologically tested and it was efficient on tumorous mice.
8) The samples obtained in steps 6 and 7, respectively were united and this material was regarded as final product.

By using identical doses of the so isolated active substance the animal experiments disclosed in the cited Hungarian and international patent applications were repeated, but the active substance was given always through the mouth (per os).

The experiments resulted in identically favorable results in case of all examined types of tumors as in case of the previous experiments carried out with the active substance taken from the blood plasma, which is understandable, since the active substances were substantially identical.

By using the method according to the invention substantially higher amounts of substance can be obtained as if the material had been taken from the blood of the same animal, furthermore the utilization of the colostrum does not cause harm to the animal.

For illustrating the quantitative proportions it should be noted that a cow with average weight can supply about 20 liters of colostrum every day in the first period following delivery that can last even up to 3-4 weeks.

The invention claimed is:

1. A method for obtaining an anti-tumor substance from the colostrum of an even-toed hoofed animal having leucosis, comprising the steps of:

a) providing colostrum from an even-toed hoofed animal having leucosis;
b) shaking the colostrum with an identical volume of a 1:1 mixture comprising i-propyl alcohol and chloroform at room temperature for 8 hours;
c) centrifuging the resulting material at a speed of at least 5000 rev/mm for 20 minutes in a cooled state to result in an upper layer, medial layer, organic layer and the rest of the material;
d) removing the upper layer and subjecting it to freeze-drying; and
e) diluting the dried upper layer in physiological saline solution to a therapeutically effective concentration of the anti-tumor substance.

2. The method of claim 1, further comprising freezing the medial layer obtained in step 4c) and diluting the medial layer in physiologic saline solution to a therapeutically effective concentration of the anti-tumor substance.

3. The method of claim 2, further comprising combining the diluted upper layer and the diluted medial layer.

4. The method of claim 1, further comprising:
f) diluting the rest of the material obtained in step 4c) with a 1:1 mixture of chloroform and benzyl alcohol to make up the original volume and shaking the material for 8 hours;
g) storing the material at a temperature of 2-40° C.;
h) centrifuging the material from step g) just as in step c) and separating the upper layer;
i) freeze drying the upper layer obtained in step h); and
j) diluting the dried upper layer in physiological saline solution to a therapeutically effective concentration of the anti-tumor substance.

5. The method of claim 4, wherein the upper layer obtained in step j) is combined with the upper layer obtained in step e).

6. The method of claim 1, wherein the animal is a cow.

* * * * *